United States Patent
Nishida et al.

(10) Patent No.: US 9,510,742 B2
(45) Date of Patent: Dec. 6, 2016

(54) INTERNAL BODY OBSERVATION DEVICE

(75) Inventors: Hiroyuki Nishida, Sagamihara (JP); Hideyuki Takaoka, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 1618 days.

(21) Appl. No.: 13/037,731

(22) Filed: Mar. 1, 2011

(65) Prior Publication Data

US 2011/0237887 A1   Sep. 29, 2011

Related U.S. Application Data

(63) Continuation of application No. PCT/JP2009/055504, filed on Mar. 19, 2009.

(30) Foreign Application Priority Data

Sep. 1, 2008 (JP) .................................. 2008-223956

(51) Int. Cl.
A61B 1/04 (2006.01)
A61B 1/06 (2006.01)
(Continued)

(52) U.S. Cl.
CPC .......... *A61B 1/0638* (2013.01); *A61B 1/00009* (2013.01); *A61B 1/00124* (2013.01);
(Continued)

(58) Field of Classification Search
CPC ............. A61B 1/043; A61B 1/06; A61B 1/07; A61B 1/0661; A61B 1/0638; A61B 1/00163; A61B 1/041; G01J 1/58; G01N 21/474; G02B 6/35
(Continued)

(56) References Cited

U.S. PATENT DOCUMENTS 6,417,950 B1 * 7/2002 Cathey, Jr. ............. H04N 9/045
                                                        348/E9.01
2013/0329224 A1 * 12/2013 Takaoka ............. A61B 1/00096
                                                        356/402

FOREIGN PATENT DOCUMENTS

JP   9-154812       6/1997
JP   09-154812 A  * 6/1997
(Continued)

OTHER PUBLICATIONS

Application No. JP 2005-275530, Publication No. 2007-082769, Sendai Tomoari, Date of Filing: Sep. 22, 2005, Applicant: Fujifilm Corp.*

(Continued)

*Primary Examiner* — John P Leubecker
*Assistant Examiner* — Rajaa El Alami
(74) *Attorney, Agent, or Firm* — Scully, Scott, Murphy & Presser, P.C.

(57) ABSTRACT

The invention relates to an internal body observation device which includes an ordinary observation light source, an ordinary observation irradiation optical system, a special observation light source, a special observation irradiation optical system, an observation optical system for transmitting the light from an observation target, a detection means configured to detect the light transmitted from the observation optical system as a detection signal, and a processing unit for separating the detection signal in the respective light sources and making the detection signal into images, wherein the light from any one of the ordinary observation light source and the special observation light source is modulated, and the modulated light can be radiated to the observation target together with the light from the other light source, and the detection signal detected by the detection means is separated by the processing unit based on the frequency of the modulation.

6 Claims, 3 Drawing Sheets

(51) Int. Cl.
  *A61B 1/05*   (2006.01)
  *A61B 1/00*   (2006.01)
  *A61B 5/00*   (2006.01)

(52) U.S. Cl.
  CPC .......... *A61B 1/00163* (2013.01); *A61B 1/041* (2013.01); *A61B 1/05* (2013.01); *A61B 1/06* (2013.01); *A61B 5/0062* (2013.01); *A61B 5/0084* (2013.01); *A61B 5/418* (2013.01)

(58) Field of Classification Search
  USPC ........................................ 600/108, 110, 178
  See application file for complete search history.

(56) References Cited

FOREIGN PATENT DOCUMENTS

| | | |
|---|---|---|
| JP | 2002-112961 A | 4/2002 |
| JP | 2007-82769 | 4/2007 |
| JP | 2007-252440 | 10/2007 |
| JP | 2007-268047 | 10/2007 |
| WO | WO 99/37204 | 7/1999 |

OTHER PUBLICATIONS

Japanese Office Action dated Sep. 10, 2013 from related Japanese Application No. 2008-223956, together with an English language translation.
International Search Report dated May 26, 2009.

\* cited by examiner

INTERNAL BODY OBSERVATION DEVICE

CROSS-REFERENCE TO RELATED APPLICATIONS

This application is a continuation of PCT International Application No. PCT/JP2009/055504, filed on Mar. 19, 2009, and is based upon and claims the benefit of priority from prior Japanese Patent Application No. 2008-223956, filed Sep. 1, 2008, the entire contents of each of which are incorporated herein by reference.

BACKGROUND OF THE INVENTION

1. Field of the Invention

The invention relates to a device for observing an internal body.

2. Description of the Related Art

An observation in a device such as an endoscope and the like for observing an internal body includes an ordinary observation by a white light source, and a special observation for performing an observation for a desired object by the irradiation from a light source other than the white light.

Conventionally, there is proposed an endoscope capable of performing two types of irradiations by a fluorescence excitation laser and a white light source for white light observation. The two types of the irradiations are detected by switching the respective irradiations by changing a timing of shutter.

Further, there is proposed also an electronic microscope device having a near-infrared light irradiation device and an irradiation means for radiating a white light. Such a device separates near-infrared light information and white light information using spectral information and determines and displays a near-infrared light irradiation position. Optical coherence tomography (OCT) is assumed as a special observation using a near-infrared light. However, when the spectral information is only used, weak scattering light information cannot be captured from a deeper target than OCT can observe.

In the observation using the conventional endoscope capable of performing the two types of the irradiations, it is necessary to switch the irradiations from the two types of the light sources at desired timing. With the configuration, the device performs the ordinary observation and the special observation. Accordingly, in the conventional device, the information obtained by the ordinary observation is offset from the information obtained by the special observation. The offset is not preferable especially when, for example, a treatment such as a surgical operation is performed using, for example, the endoscope capable of performing the two types of the irradiations.

BRIEF SUMMARY OF THE INVENTION

Thus, according to an aspect of the invention, an object of the invention is to provide an internal body observation device capable of performing an observation by two light sources preventing an offset of information as well as separating undesirable noise from a desired signal, in particular, capable of performing an ordinary observation and a special observation highly sensitively.

According to an aspect of the invention, there is provided an internal body observation device which includes an ordinary observation light source, an ordinary observation irradiation optical system, a special observation light source, a special observation irradiation optical system, an observation optical system for transmitting the light from an observation target, a detection means configured to detect the light transmitted from the observation optical system as a detection signal, and a processing unit for separating the detection signal in the respective light sources and making the detection signal into images, wherein the light from any one of the ordinary observation light source and the special observation light source is modulated, and the modulated light can be radiated to the observation target together with the light from the other light source, and the detection signal detected by the detection means is separated by the processing unit based on the frequency of the modulation.

According to an aspect of the invention, there is provided an internal body observation device capable of performing an observation by two light sources preventing an offset of information as well as separating undesirable noise from a desired signal, in particular, capable of performing an ordinary observation and a special observation highly sensitively.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
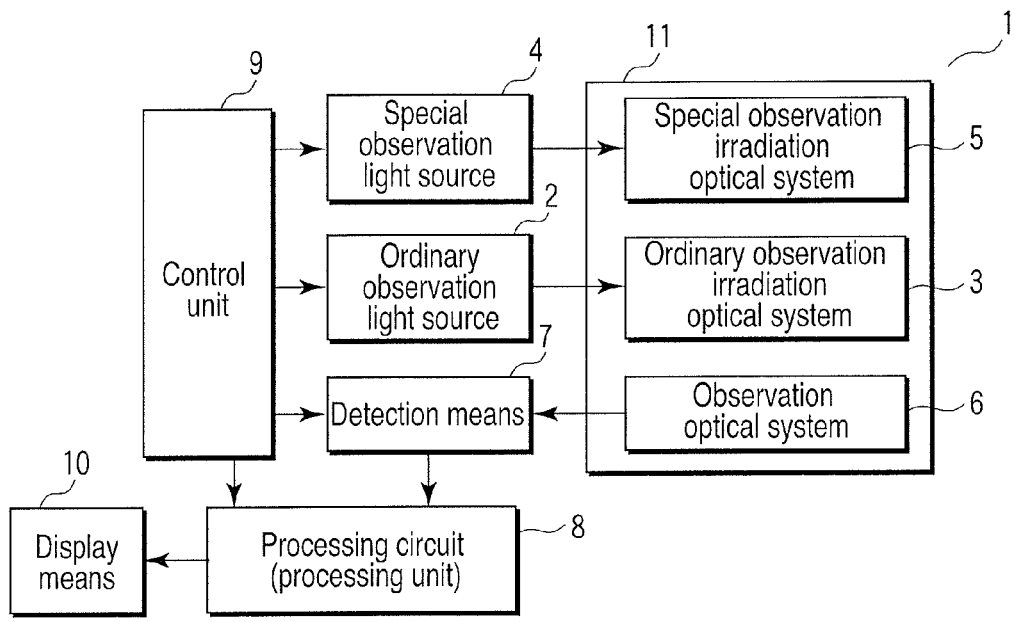
FIG. 1 is a view showing a first embodiment.

An internal body observation device according to the invention is a device which includes two types of light sources, i.e., an ordinary observation light source for supplying a irradiation light for ordinary observation and a special observation light source for supplying a irradiation light for special observation and in which the light from one of the light sources is relatively modulated to the light from the other light source and can be radiated together with the unmodulated light from the other light source.

"The internal body observation device" in the invention is a device such as an endoscope, an in vivo imaging microscope, and the like for observing an internal body. Any of the devices are included in the invention.

Here, a term "ordinary observation" means an observation (watching an image and/or measurement) by a white light. A term "special observation" means an observation (watching an image and/or measurement) making use of a light source other than the white light for performing a desired observation (watching an image and/or measurement). The light source may be any of known light sources capable of radiating, for example, a red light, a blue light, infrared rays, near infrared rays, or a fluorescence excitation light.

It is only necessary that the modulation in the invention be performed at a predetermined cycle as to a degree of intensity, that is, as to a tone of light. The light to be modulated may be either light from the ordinary observation light source or light from the special observation light source. However, since the sensitivity of light is improved by being modulated and separated, it is preferable to perform modulation to the special observation light source. The modulation may be performed by increasing and decreasing the output of the light source, may be performed using a device for periodically increasing and decreasing transmittance in a irradiation optical system, or may be performed using any of known modulation means.

Here a term "not modulated" or "unmodulated" means that only the light from any one light source of the ordinary observation light source and the special observation light source is modulated and the light from the other light source is not relatively modulated. Accordingly, the term does not restrict the state of light to the state that no modulation is performed. As described later, plural modulated lights having different modulation conditions may be rather radiated together to a irradiation target as the lights from the special observation light source and/or the ordinary observation light source, and the device may be configured to perform the above irradiation.

A term "can be radiated together" in the paragraph that a modulated light and an unmodulated light can be radiated together to an observation target indicates that the lights from the two light sources may be radiated to the observation target at the same time, may be radiated with time difference, or may be radiated independently. For example, that the modulated light and the unmodulated light "can be radiated together" to the observation target means that it is preferable that the lights from the two light sources be radiated to an observation target at the same time in an observation device such as an endoscope in which the positional relation of the device to the observation target changes at all times. When a high speed light scanning means is used or when an observation target is made unmovable on an observation stage as in a microscope, lights may be radiated to the observation target with some time lag. Even when the time lag is employed as described above, since the ordinary observation can be caused to correspond to the special observation, the irradiation is applied to "can be radiated together". Further, the lights from the two light sources may be radiated from the same outgoing end or from different outgoing ends via separate irradiation means or separate irradiation light paths.

Further, a surface sequential light emitting source for sequentially emitting the three primary colors may be used as the ordinary observation light source. In this case, it is only necessary to sequentially radiate the lights of the three primary colors and the light from the special observation light source to the observation target. For example, in a sequential light emission, the lights which compose the three primary colors, for example, a red light (R), a green light (G), and a blue light (B) may be sequentially and repeatedly emitted in any order. In the observation making use of the surface sequential light emission, the light from the special observation light source may be further added to the sequence of emission of the three primary colors, and the lights may be sequentially radiated to the observation target. Also in the observation performed by the surface sequential light emission, the light from the special observation light source can be separated by being modulated. Further, the ordinary observation performed by the surface sequential light emission can be performed by any of known methods.

Further, the internal body observation device according to the invention may include an observation optical system for transmitting the light from an observation target which receives the ordinary observation irradiation light and the irradiation light for special observation, a detection means configured to detect the light transmitted from the observation optical system as a detection signal, and a processing unit for separating the detection signal detected by the detection means in the respective light sources and making the detection signal into images.

Although an optical fiber is preferably used as the observation optical system, the observation optical system is not limited to the optical fiber and may include a relay lens.

The detection means may include an image pickup element which may be an imager as any of known surface detection means, for example, a CCD image sensor or a CMOS image sensor, and otherwise may be a point detection means such as any of known photodetectors or photomultiplier tubes.

In imaging, when the point detection means which is suitable for point detection such as the photodetector or the photomultiplier tube is used, the imaging may be performed by combining the point detection means with a scanning means for scanning a detection region on an observation target to which a light is irradiated from a light source, the scanning being carried out through controlling of the detection region or the light.

The scanning means may be a mirror scanning means configured using a mirror such as a galvano mirror, and when an optical fiber is used in the observation optical system, the scanning means may be a fiber scanning means configured to scan an irradiation light over an entire detection region by vibrating the optical fiber itself. When the scanning means is used, a CCD and a CMOS, which are image pickup elements for performing surface detection, also may be used while scanning through operating of only the irradiation light, to receive a light from a light receiving scope corresponding the detecting region sequentially, and then to construct an image. The detection region means a region on the surface of the observation target to which light is radiated by the light source.

The processing unit may be a process circuit constructed by a processor and software. In the device, after the lights are radiated from the two types of the light sources to the observation target while one of which is modulated and the other of which is not modulated, the lights pass via the observation optical system and detected by the detection means as a detection signal. It is only necessary that the detection be performed using a sampling cycle sufficiently shorter than the time of one cycle of the frequency of the detection as a detection time so that a sampling theorem is satisfied. That is, it is only necessary to perform two or more samplings per cycle in time series. It is only necessary that the processing unit configure an image by using only the same frequency component as a modulated frequency in the frequency component of a time series signal obtained by the detection means. Further, the range of the modulated frequency will be determined depending on the performance of the imager being used.

Further, the internal body observation device according to invention may include the special observation light source, the ordinary observation light source, the detection means, a control unit for controlling the processing unit, and a display means for displaying an image obtained by the processing unit.

It is only necessary for the control unit to include a processor and a storage means. The processor may be, for example, a CPU or the like, and the storage means may be any of known storage means configured to store information such as a program and data. Another storage means may be connected to the control unit to input and output information. Further, the control unit may be a control device of a computer or the like to which software for executing the control is previously installed.

The display means may be any of known display means capable of displaying an image such as a display or a printer.

An embodiment of the invention will be explained according to the drawings. Note that, in the following explanation, components having approximately the same function and configuration are denoted by the same reference numerals, and a duplicate explanation will be given only when necessary.

<First Embodiment>

FIG. 1 is a schematic functional block diagram of an internal body observation device 1 according to a first embodiment of the invention. As shown in FIG. 1, the internal body observation device 1 includes an ordinary observation light source 2, an ordinary observation irradiation optical system 3, a special observation light source 4, a special observation irradiation optical system 5, an observation optical system 6, a detection means 7, a process circuit 8, a control unit 9, and a display means 10.

The ordinary observation light source 2 and the special observation light source 4, the detection means 7, the control unit 9 as well as the display means 10 may be the components described above. The process circuit 8 may be, for example, the component described above in the processing unit.

The observation optical system 6 is an optical system for transmitting the lights, which are radiated from the ordinary observation light source 2 and the special observation light source 4 to an observation target and reflected from the observation target, to the detection means 7. After one of the lights from the ordinary observation light source 2 and the special observation light source 4 is modulated, the lights are radiated to the observation target via the ordinary observation irradiation optical system 3 and the special observation irradiation optical system 5, respectively. The lights reflected from the observation target are collected to the detection means 7 via the observation optical system 6. The observation optical system 6 may be the component as described above, that is, may be the optical fiber and may be the relay lens.

The ordinary observation irradiation optical system 3 is an optical system for transmitting the light radiated from the ordinary observation light source 2 to the observation target, and the special observation irradiation optical system 5 is an optical system for transmitting the light radiated from the special observation light source 4 to the observation target. The ordinary observation irradiation optical system 3 and the special observation irradiation optical system 5 may be optical fibers or relay lenses. Alternatively, the ordinary observation irradiation optical system 3 and the special observation irradiation optical system 5 may include lenses and/or mirrors and/or prisms and/or diffraction gratings, and the like.

When a laser beam and the like whose luminous flux is previously narrowed is used as the light source, the ordinary observation irradiation optical system 3 and/or the special observation irradiation optical system 5 need not be used, and a detection region on which an irradiation light is impinged may be restricted using a mask and the like. The detection region means a region on the surface of the observation target to which a light is radiated by the light source.

The ordinary observation irradiation optical system 3, the special observation irradiation optical system 5, and the observation optical system 6 are disposed in, for example, a holder 11. The internal body observation device 1 is used by, for example, inserting the holder 11 portion into the body. When the ordinary observation light source 2 and the special observation light source 4 are disposed in a portion nearest an observation target of the holder 11, the ordinary observation irradiation optical system 3 and the special observation irradiation optical system 5 can be omitted.

Next, an example of observation (watching an image and/or measurement) performed using the internal body observation device 1 will be explained.

(1) A signal having a frequency condition to be used is output from the control unit 9 to the special observation light source 4 and the processing unit 8;

(2) A modulated light having a frequency based on the frequency condition is generated from the special observation light source 4 and radiated to the observation target;

(3) An unmodulated light is generated from the ordinary observation light source 2 and radiated to the observation target;

(4) The light reflected from the observation target is detected by the detection means 7 via the observation optical system 6;

(5) The detection signal detected at the step (4) is output to the processing unit 8 as data;

(6) The processing unit 8 processes the signal input at the step (5) based on the frequency condition input from the control unit 9 at the step (1);

(a) An image is configured as a special observation image by extracting only a component corresponding to the frequency output from the control unit 9;

(b) An image is configured as an ordinary observation image by extracting only a bias component, and (7) An ordinary observation and a special observation can be performed on the observation target without generating an offset of information by displaying the images obtained at the step (6) on the display means 10. With the operation, a desired observation and observation can be performed with high sensitivity.

Here, it is only necessary that the step (1) be performed before the irradiation from the special observation light source at the step (2). Further, any of the irradiation from the special observation light source 4 and the irradiation from the ordinary observation light source 2 may be performed first or second or both the irradiations may be performed at the same time. At the step (6)-(b), an image may be configured of data obtained by subtracting the component used at the step (6)-(a) from raw data.

Further, at the step (7), the images obtained at the step (6)-(a) and the step (6)-(b) may be displayed separately on the display means 10. Alternatively, at the step (7), after another image is synthesized by overlapping the images obtained at the step (6)-(a) and the step (6)-(b) by the processing unit 8, the another image may be displayed.

Further, a table and the like, which cause the frequency condition, the detected detection signal, the detection signals before and after they are processed, the extracted signal, the configured images such as the special observation image and the ordinary observation image, as well as the program and plural pieces of information to correspond to each other, may be stored in a storage means connected to input and output information independently of the storage means included in the control unit 9 and/or the control unit and/or the information may be recorded in the storage means.

Further, although the example for modulating the light from the special observation light source 4 is shown here, the modulation may be performed on the light from the ordinary observation light source 2. In the case, it is only necessary that the light from the special observation light source 4 be extracted as a bias component, and the light from the ordinary observation light source 2 be extracted based on a signal as to frequency information which is output from the control unit 9 and used, as a component corresponding to the frequency.

The observation (watching an image and/or measurement) method is also included in the scope of the invention.

<Second Embodiment>

Figure 2:
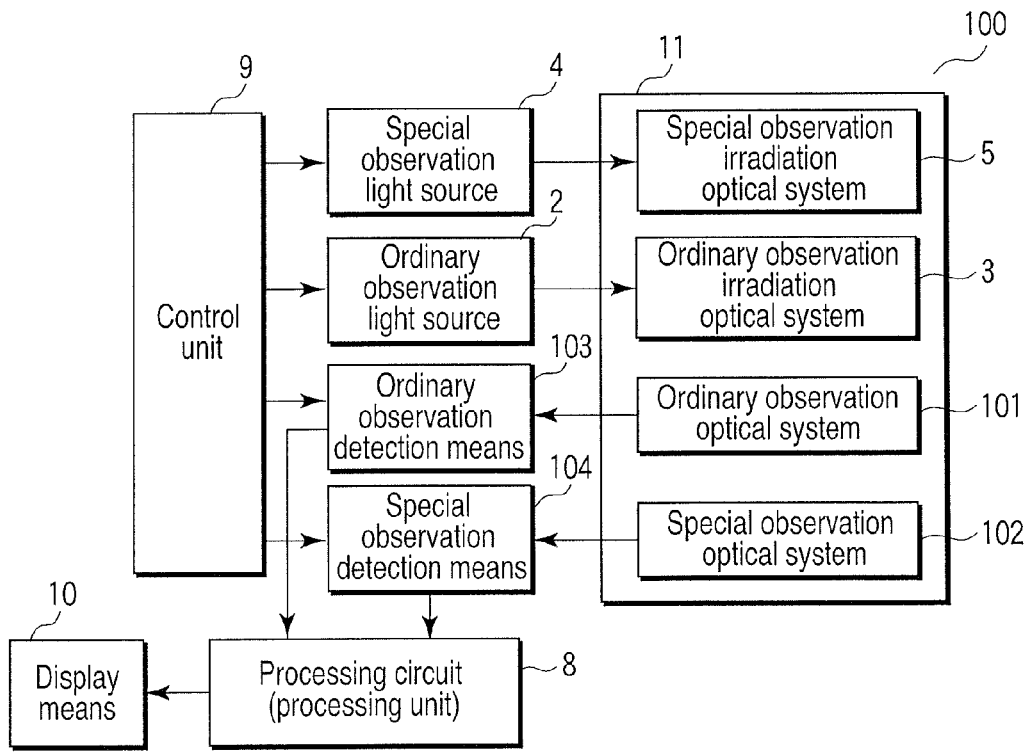
FIG. 2 is a view showing a second embodiment.

FIG. 2 is a schematic functional block diagram of an internal body observation device 100 according to a second embodiment of the invention. The internal body observation device 100 shown in FIG. 2 is the same as the internal body observation device 1 shown in FIG. 1 except that the observation optical system 6 of FIG. 1 is replaced with an ordinary observation optical system 101 and a special observation optical system 102 and that the detection means 7 is replaced with an ordinary observation detection means 103 and a special observation detection means 104.

The ordinary observation detection means 103 and the special observation detection means 104 may be the same component as the detection means described above.

An example for performing observation by the internal body observation device 100 will be explained below.

(1) A signal having a frequency condition to be used is output from a control unit 9 to a special observation light source 4 and a processing unit 8;
(2) A modulated light having a frequency based on the input frequency condition is generated from the special observation light source 4 and radiated to an observation target;
(3) An unmodulated light is generated from an ordinary observation light source 2 and radiated to the observation target;
(4) The light reflected from the observation target is transmitted via the special observation optical system 102 and the ordinary observation optical system 101 and detected by the special observation detection means 104 and the ordinary observation detection means 103;
(5) The respective detection signals detected by the ordinary observation detection means 103 and the special observation detection means 104 are output to the processing unit 8 as data;
(6) The processing unit 8 processes the signals input at the step (5) based on the frequency condition output at the step (1);
    (a) An image is configured as a special observation image by extracting only a component corresponding to the input frequency to the data from the special observation detection means 104;
    (b) An image is configured as an ordinary observation image by extracting only a bias component to the data from the ordinary observation detection means 103; and
(7) The image obtained at the step (6) is displayed on the display means 10. With the steps, an ordinary observation and a special observation can be performed on the observation target without causing an offset of information.

With the operation, a desired observation and observation can be performed with high sensitivity.

Here, it is only necessary that the step at (1) be performed before the irradiation from the special observation light source 4 at the step (2). Further, any of the irradiation from the special observation light source 4 and the irradiation from the ordinary observation light source 2 may be performed first or second or both the irradiations may be performed at the same time. At the step (6)-(b), an image may be configured of data obtained by subtracting the component used at the step (6)-(a) from raw data. Further, at the step (7), the images obtained at the step (6)-(a) and the step (6)-(b) may be displayed separately on the display means 10. Alternatively, at the step (7), after another image is synthesized by overlapping the images obtained at the step (6)-(a) and the step (6)-(b) by the processing unit 8, the another image may be displayed.

Further, although the example for modulating the light from the special observation light source 4 is shown here, the modulation may be performed on the light from the ordinary observation light source 2. In the case, it is only necessary to extract the light reflected from the observation target derived from the special observation light source 4 as a bias component. Further, it is only necessary to extract the light, which is derived from the ordinary observation light source 2 and reflected from the observation target, based on a signal as to frequency information, which is output from the control unit 9 and used, as a component corresponding to the frequency.

The observation (watching an image and/or measurement) method is also included in the scope of the invention.

<Third Embodiment>

Figure 3:
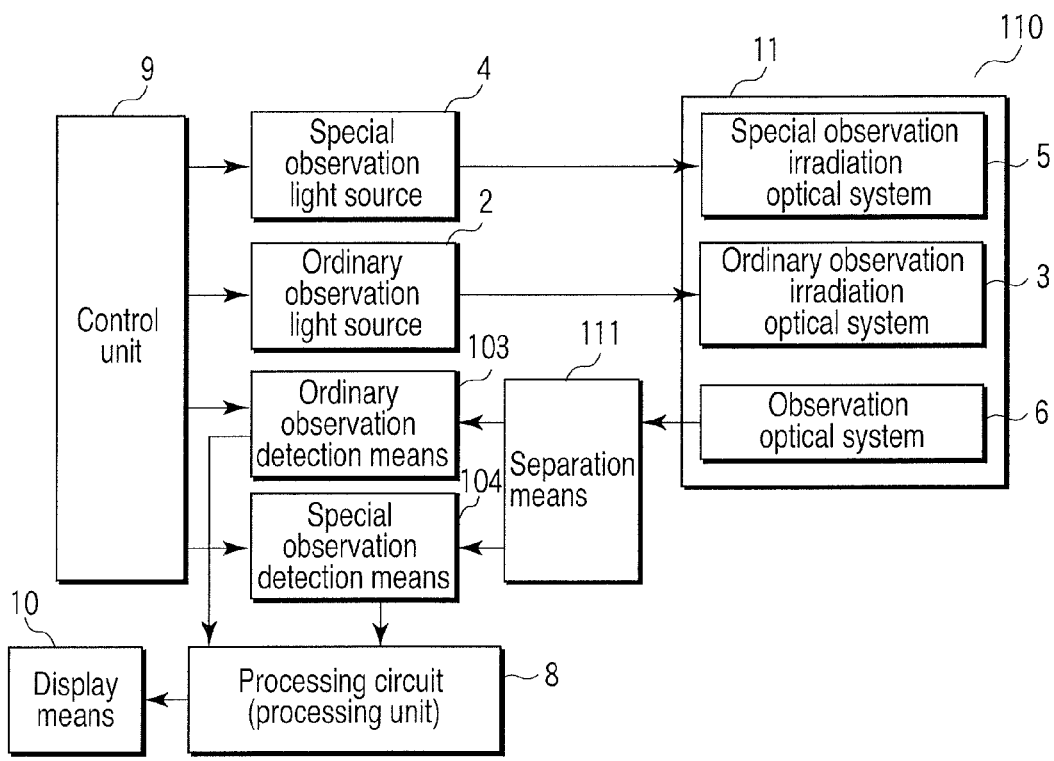
FIG. 3 is a view showing a third embodiment.

FIG. 3 is a schematic functional block diagram of an internal body observation device 110 according to a third embodiment of the invention. The internal body observation device 110 shown in FIG. 3 is the same as the internal body observation device 1 shown in FIG. 1 except that the detection means 7 of FIG. 1 is replaced with an ordinary observation detection means 103 and a special observation detection means 104 and further a separation means 111 is interposed between the ordinary observation detection means 103 and the special observation detection means 104, and an observation optical system 6.

Figure 4:
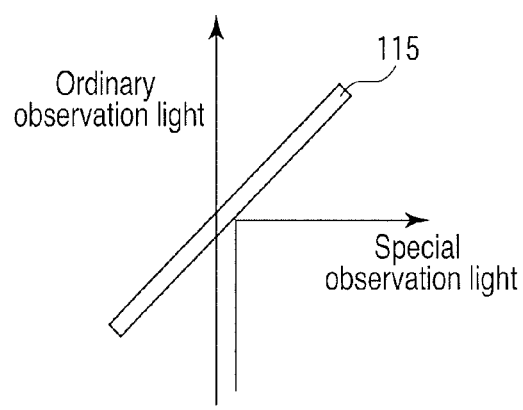
FIG. 4 is a view showing an example of a separation means.

The separation means 111 is a means for separating light (that is, an ordinary observation light) which is transmitted via the observation optical system 6, reflected on an observation target and derived from an ordinary observation light source 2 and light (that is, a special observation light) which is reflected by the observation target and derived from the special observation light source 4. The separation means 111 may be any of known means capable of separating a modulated light and an unmodulated light. The separation means 111 may be, for example, a reflection filter having wavelength selection characteristics or may be a polarization beam splitter or the like when a polarized light is used. An example of separation using a reflection filter is shown in FIG. 4. An ordinary observation light passes through a reflection filter 115, and a special observation light is reflected on the reflection filter 115. It is only necessary that the reflection filter 115 be configured such that, in the light passed through the reflection filter 115, an ordinary observation light is detected by the ordinary observation detection means 103 and a special observation light is detected by the special observation detection means 104 by any of known optical systems, for example, a mirror and/or a lens.

An example in which an observation (watching an image and/or measurement) is performed by the internal body observation device 110 will be explained below.

(1) A signal having a frequency condition to be used is output from a control unit 9 to the special observation light source 4 and a processing unit 8;
(2) A modulated light having a frequency based on the frequency condition is generated from the special observation light source 4 and radiated to the observation target;
(3) An unmodulated light is generated from the ordinary observation light source 2 and radiated to the observation target;
(4) The light reflected from the observation target is transmitted via the observation optical system 6 and separated by the separation means 111;
(5) The respective detection signals detected by the ordinary observation detection means 103 and the special observation detection means 104 are output to the processing unit 8 as data;
(6) The processing unit 8 processes the signal input at the step (5) based on the frequency condition input from the control unit 9 at the step (1);
    (a) An image is configured as a special observation image by extracting only a component corresponding to the given frequency to the data from the special observation detection means 104;
    (b) An image is configured as an ordinary observation image by extracting only a bias component to the data from the ordinary observation detection means 103; and
(7) The images obtained at the step (6) are displayed on the display means 10. With the steps, an ordinary observation and a special observation can be performed on the observation target without causing an offset of information. With the operation, a desired observation and observation can be performed with high sensitivity.

Here, the light separated by the separation means 111 is configured such that (a) the special observation light is detected by the special observation detection means, and (b) the ordinary observation light is detected by the ordinary observation detection means.

Here, it is only necessary that the step (1) be performed before the irradiation from the special observation light source at the step (2). Further, any of the irradiation from the special observation light source 4 and the irradiation from the ordinary observation light source 2 may be performed first or second or both the irradiations may be performed at the same time. At the step (6)-(b), it is only necessary that an image be configured of data obtained by subtracting the component used at the step (6)-(a) from raw data. Further, at the step (7), the images obtained at the step (6)-(a) and the step (6)-(b) may be displayed separately on the display means 10. Alternatively, at the step (7), after another image is synthesized by overlapping the images obtained at the step (6)-(a) and the step (6)-(b) by the processing unit 8, the another image may be displayed.

Further, although the example for modulating the light from the special observation light source 4 is shown here, the modulation may be performed on the light from the ordinary observation light source 2. In this case, it is only necessary to extract the light reflected on the observation target and derived from the special observation light source 4 as a bias component and to extract the light reflected on the observation target and derived from the ordinary observation light source 2 as the component corresponding to the given frequency.

Further, since the signal is separated at the step (4), the step (6) may be arbitrarily employed. When, for example, the signal is insufficiently separated by the separation means 111, the step (6) more effectively functions.

The observation (watching an image and/or measurement) method is also included in the scope of the invention.

<Fourth Embodiment>

Figure 5:
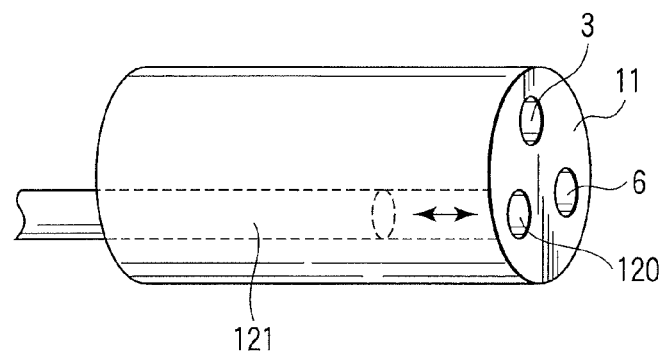
FIG. 5 is a view showing a part of a fourth embodiment.

FIG. 5 shows a part of a fourth embodiment. The fourth embodiment is, as shown in part in FIG. 5, a mode which makes use of a conventional endoscope including an ordinary observation irradiation optical system 3 and an observation optical system 6 in a holder 11. An internal body observation device according to the mode is configured such that a forceps port 120 of the endoscope is additionally provided with a special observation irradiation optical system 121, that is, the internal body observation device is an add-on type internal body observation device. The internal body observation device including the holder 11 in that case may be shown by a functional block diagram as shown in FIG. 1 in its entirety as well as may perform an observation in the procedure shown in the first embodiment.

In this case, it is preferable to store ordinary observation (watching an image and/or measurement) information and special observation (watching an image and/or measurement) information in a processing unit 8 and to display the information on a display means 10 when forceps (not shown) for performing a desired treatment is inserted into the body from the forceps port 120.

Alternatively, another embodiment may be a mode shown in a functional block diagram as shown in FIG. 2. That is, the another embodiment is a mode which makes use of a conventional endoscope including an ordinary observation irradiation optical system, an observation optical system, and a forceps port, in which case the endoscope is added with a special observation irradiation optical system and a special observation optical system in the holder 11. The internal body observation device including the holder 11 is shown by a functional block diagram as shown in FIG. 2 in its entirety and performs an observation in the procedure shown in the second embodiment. The internal body observation device shown in the functional block diagram as shown in FIG. 2 may be added with a special observation irradiation optical system. Even in this case, it is only necessary that an observation be performed in the procedure shown in the second embodiment.

Even with such a configuration, an ordinary observation and a special observation can be performed on an observation target without generating an offset of information. With the operation, a treatment using the forceps can be properly performed in real time while performing a desired observation and observation with high sensitivity via the display means 10.

<Fifth Embodiment>

A fifth embodiment will be explained below. The embodiment is an example in which near infrared rays which are light modulated for a special observation (watching an image and/or measurement) are used and a scattered image is pickup up and, at the same time, an ordinary observation (watching an image and/or measurement) is performed using an unmodulated white light in an noncontact state with a living body using the internal body observation device 1 shown in the first embodiment.

A special observation light source 4 may be a laser, a semiconductor LD, an LED and an SLD or an ordinary lamp light source may be used. Further, the light from the special observation light source is modulated at a predetermined cycle. Further, it is only necessary that the wavelength of the light from the special observation light source be a wavelength longer than, for example, 750 nm. It is only necessary that the wavelength be, for example, 750 to 950 nm to specify the position of a blood vessel.

Figure 6:
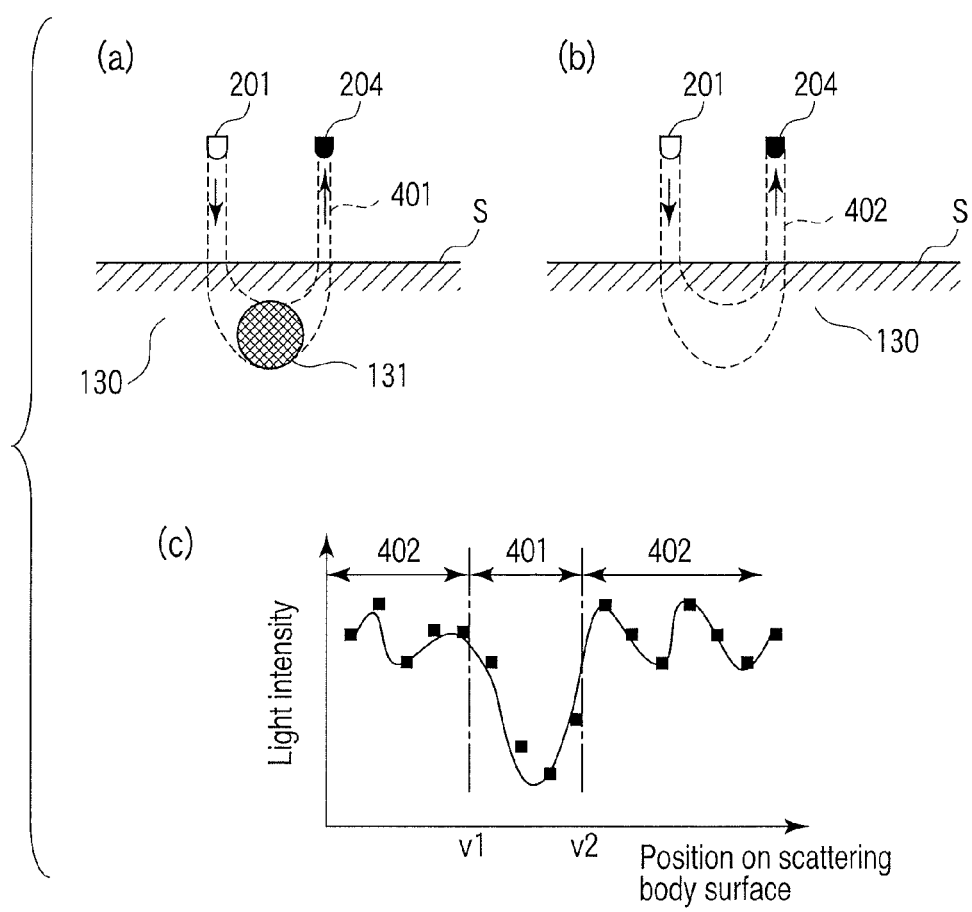
FIG. 6 is a view having schematic views showing how a backscattered light is detected via a scattering medium and the light intensity data of the backscattered light is obtained.

FIG. 6 is a view having schematic views showing how a backscattered light, which is light modulated via a scattering medium when a special observation is performed, is detected and how the light intensity data of the backscattered light is obtained, and the special observation irradiation optical system 5 shown in FIG. 1 is omitted in the configuration for performing the special observation. FIG. 6 (a) shows a case where a heterogeneous portion 131 whose absorption is larger than that of a scattering medium 130, exists in a scattering body S. The modulated light radiated by a special observation light source 201 is attenuated by the influence of the heterogeneous portion 131, an attenuated backscattered light 401 is detected by a detection means 204, and the light intensity data of the backscattered light 401 is obtained. Here, the light intensity data, which is detected in the case as shown in FIG. 6 (a) is called heterogeneous portion influence dominant data or a heterogeneous portion detection signal. In contrast, FIG. 6 (b) is a view showing the case where the heterogeneous portion 131 does not exist in the scattering body S. In this case, the modulated light radiated by the special observation light source 201 is not attenuated, a backscattered light 402 scattered by the scattering medium 130 is detected by the detection means 204, and the light intensity data of the backscattered light 402 is obtained. Here, the light intensity data detected in the case as shown in FIG. 6 (b) is called scattering medium influence dominant data or a scattering medium detection signal.

When, for example, the scattering body S as shown in FIGS. 6A and 6B is continuously detected at different positions on the scattering body S by a time sequential image pick-up or a light scan, a light intensity graph as shown in FIG. 6 (c) is obtained. In the graph, the light intensity data 402, in which the influence of the scattering medium 130 is dominant, and the light intensity data 401, in which the influence of the heterogeneous portion is dominant, exist. Accordingly, when the data 402 and 401 are observed, two signals having different intensities are detected. The existence of the heterogeneous portion 131 in the scattering body S can be detected making use of the difference in intensity.

On the other hand, the light from an ordinary observation light source 2, which is radiated simultaneously with the modulated light, is radiated on the surface of the scattering body S at the same time from an ordinary observation irradiation optical system 3 having a irradiation light path and a irradiation end portion different from those of a special observation irradiation optical system 121 as in the endoscope which has been explained in the fourth embodiment and shown in FIG. 5.

Here, as shown in FIG. 5, since a light irradiation end portion for the ordinary observation and a light irradiation end portion for the special observation are disposed on the same surface of an endoscope as an observation device, the respective lights, which are radiated at the same time, are detected in the same distance at the same time. As described above, the light from the ordinary observation light source 2 and the light from the special observation light source 201, which are radiated to the scattering body S as an observation target at the same time, are detected by a detection means 7 at the same time via an observation optical system 6. After the processing unit 8 separates the detected light depending on whether or not the detected light is modulated and constructs the image obtained by the ordinary observation and the image obtained by the special observation separately, the processing unit 8 synthesizes an image in which the separate images are overlapped and displays the synthesized image on a display means 10.

With the configuration, the ordinary observation and the special observation can be performed on the observation target without contact with a living body and without generating either an offset in time or an offset in space to information. With the operation, a desired observation (watching an image and/or measurement) and observation (watching an image and/or measurement) can be performed at the same time with high sensitivity.

The positions of a blood vessel, a lymph channel or a nerve in a tissue, for example, a smooth muscle or a fat can be specified by the special observation (watching an image and/or measurement) making use of the backscattered light. According to a mode of the invention, it is possible to specify the position of a blood vessel and the like and to perform the ordinary observation (watching an image and/or measurement) by the white light at the same time. As a result, the information in a scattering body by the special observation and the information of the surface of the scattering body by the ordinary observation can be obtained without including an offset in time. Therefore, even if a living body and/or the observation device itself moves, the images of respective observed lights can be caused to agree with each other on the display means 10 at all times. As a result, a more appropriate treatment can be performed in real time by a prompt and correct determination. Further, when the same detection region is observed in a range of desired field of view in time series and when a heterogeneous portion and the like move and are deformed in shape in a living body, there is an advantage in that the relative movement in the living body can be caused to accurately correspond to each other on the display means 10 and a correct observation can be continued.

Further, the information as to the obtained special observation light, is separated according to the frequency condition. With the operation, noise can be reduced, and the special observation can be performed with high sensitivity. Further, since the noise is reduced, the information as to a weak scattering light derived from a deeper heterogeneous material can be also obtained with highly sensitively. With the configuration, since detection data or an image can be obtained according to the composition and the density of the heterogeneous portion 131, identification can be performed more accurately than with a conventional device. Further, the internal body observation device may be improved so as to be configured to detect different types of heterogeneous portions by simultaneously radiating modulated lights having different modulation conditions into a scattering body by the special light source 4 and the special observation irradiation optical system 5 as well as by separating the modulated lights according to the respective modulation conditions by the processing unit 8.

When a highly sensitive special observation is performed, it is preferable to sequentially synthesize the image information from many partial irradiation regions and to make the information into an image by illuminating a partial irradiation region smaller than an irradiation region corresponding to a finally configured image area using a light source having a strong directionality such as a laser and a semiconductor LD as well as detecting a partial detection region corresponding to the partial irradiation region using a detection means optimum for a point detection such as a photodetector or a photomultiplier tube as the detection means and scanning both the partial irradiation region and the partial detection region as to an entire irradiation region. This is because when the irradiation region and the detection region are large, a blood vessel, a lymph channel or a nerve is liable to be influenced by noise which is detected without passing through the target when the position of the blood vessel, the lymph channel or the nerve is specified. The scanning means may be a mirror scanning means such as a galvano mirror or may be a fiber scanning means for scanning an irradiation light by vibrating an optical fiber itself in the irradiation region using the optical fiber as described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An internal body observation device comprising:
   a control unit that:
      controls a first light source to radiate white light that is not modulated to an observation target; and
      controls a second light source to radiate an irradiation light different from the white light to the observation target,
      wherein the control unit controls the second light source to modulate the irradiation light at a modulation frequency, and
      wherein the control unit controls the first light source and the second light source to radiate the white light and to radiate the irradiation light at the same time;
   an observation optical system that transmits a light from the observation target irradiated by the white light and the modulated irradiation light;
   a detection unit that detects the light transmitted by the observation optical system and that outputs a detection signal based on the detected light; and
   a processing unit that:
      generates a white light image by extracting a bias component of the detection signal; and
      generates a special observation image by extracting a component of the detection signal corresponding to the modulation frequency.

2. The internal body observation device according to claim 1, further comprising a display unit that displays the special observation image generated by the processing unit.

3. The internal body observation device according to claim 1, wherein the modulated irradiation light is modulated depending on the degree of intensity of light.

4. The internal body observation device according to claim 1,
   wherein the detection unit comprises an image pickup element, and
   wherein a sampling cycle of the detection unit is sufficiently shorter than a time of a cycle determined by the modulation frequency.

5. The internal body observation device according to claim 4, wherein the detection signal is obtained by the detection unit in time series, and the special observation image is generated using only the same frequency component as the modulation frequency in the frequency components of the time series signal obtained by the processing unit.

6. The internal body observation device according to claim 1, further comprising:
   the second light source; and
   a special observation optical system that transmits the modulated irradiation light.

* * * * *